(12) United States Patent
Oloffson Ranta et al.

(10) Patent No.: US 10,425,301 B2
(45) Date of Patent: Sep. 24, 2019

(54) DATA CAPTURE AND MANAGEMENT SYSTEM

(71) Applicant: SCA Hygiene Products AB, Göteborg (SE)

(72) Inventors: Christer Oloffson Ranta, Västra Frölunda (SE); Sofia Hermansson, Västra Frölunda (SE); Anna Granberg, Oslo (NO)

(73) Assignee: ESSITY HYGIENE AND HEALTH AKTIEBOLAG, Göteborg (SE)

( * ) Notice: Subject to any disclaimer, the term of this patent is extended or adjusted under 35 U.S.C. 154(b) by 0 days.

(21) Appl. No.: 14/787,283

(22) PCT Filed: Apr. 30, 2013

(86) PCT No.: PCT/EP2013/059037
§ 371 (c)(1),
(2) Date: Oct. 27, 2015

(87) PCT Pub. No.: WO2014/177200
PCT Pub. Date: Nov. 6, 2014

(65) Prior Publication Data
US 2016/0134497 A1    May 12, 2016

(51) Int. Cl.
*H04L 12/26* (2006.01)
*H04L 29/08* (2006.01)
(Continued)

(52) U.S. Cl.
CPC ............ *H04L 43/08* (2013.01); *G16H 40/63* (2018.01); *G16H 40/67* (2018.01); *H04L 67/12* (2013.01); *H04W 84/12* (2013.01)

(58) Field of Classification Search
None
See application file for complete search history.

(56) References Cited

U.S. PATENT DOCUMENTS 6,373,395 B1 * 4/2002 Kimsey ............... A61F 13/42
                                                    340/573.5
7,250,547 B1    7/2007 Hofmeister et al.
(Continued)

FOREIGN PATENT DOCUMENTS

CN    101506802 A    8/2009
CN    101937487 A    1/2011
(Continued)

OTHER PUBLICATIONS

Korean Office Action dated Oct. 19, 2016 issued in corresponding Korean patent application No. 10-2015-7030539 (5 pages) and its English-language translation thereof (7 pages).
(Continued)

*Primary Examiner* — Thomas J Dailey
(74) *Attorney, Agent, or Firm* — Drinker Biddle & Reath LLP (57) ABSTRACT

A data capture and management system for providing an absorbent article, such as a diaper, a sanitary towel, an incontinence garment, a medical dressing and the like, with sensing and/or data logging capabilities is provided. The system includes a data logger configured to be detachably attached to or located in the vicinity of an absorbent article, a data link between the data logger and a data collection hub, and a user interface for permitting an operator to access the data collection hub from a remote location. For ease of identification, each data logger is provided with a user-friendly identifier, and the data collection hub includes a correlator that correlates the user-friendly identifier of the data logger with an IMEI number or other unique device identifier of that data logger. A method of capturing and managing incontinence data using the above system is also provided.

20 Claims, 3 Drawing Sheets

(51) Int. Cl.
*H04W 84/12* (2009.01)
*G16H 40/63* (2018.01)
*G16H 40/67* (2018.01)

(56) References Cited

U.S. PATENT DOCUMENTS

| | | | |
|---|---|---|---|
| 7,348,895 B2* | 3/2008 | Lagassey | G07C 5/008 340/907 |
| 7,977,529 B2 | 7/2011 | Bergman et al. | |
| 8,350,706 B2 | 1/2013 | Wegelin et al. | |
| 8,394,074 B2 | 3/2013 | Piette et al. | |
| 8,554,184 B2 | 10/2013 | Del Gallo et al. | |
| 8,628,506 B2 | 1/2014 | Ales, III et al. | |
| 2005/0046578 A1* | 3/2005 | Pires | A61F 13/42 340/573.5 |
| 2005/0156744 A1 | 7/2005 | Pires | |
| 2007/0203727 A1 | 8/2007 | Moore | |
| 2008/0070495 A1 | 3/2008 | Stricklen et al. | |
| 2008/0243099 A1 | 10/2008 | Tippey et al. | |
| 2008/0278336 A1* | 11/2008 | Ortega | A61B 5/1113 340/573.5 |
| 2009/0222679 A1 | 9/2009 | Lee | |
| 2011/0078779 A1 | 3/2011 | Liu et al. | |
| 2011/0222492 A1* | 9/2011 | Borsella | H04W 74/002 370/329 |
| 2011/0263952 A1 | 10/2011 | Bergman et al. | |
| 2011/0269424 A1 | 11/2011 | Multer et al. | |
| 2011/0295619 A1 | 12/2011 | Tough | |
| 2012/0206265 A1 | 8/2012 | Solazzo et al. | |
| 2012/0268278 A1 | 10/2012 | Lewis et al. | |
| 2013/0043983 A1* | 2/2013 | Lee | G06K 1/18 340/10.51 |

FOREIGN PATENT DOCUMENTS

| | | |
|---|---|---|
| CN | 102509030 A | 6/2012 |
| ES | 1053333 | 4/2003 |
| JP | 2005-153465 A | 6/2005 |
| JP | 2007-275411 A | 10/2007 |
| JP | 2010-503444 | 2/2010 |
| JP | 2010-069193 A | 4/2010 |
| JP | 2012-105839 A | 6/2012 |
| JP | 2013-509280 | 3/2013 |
| RU | 2518209 C2 | 6/2014 |
| WO | WO-96/14813 A1 | 5/1996 |
| WO | WO-00/00144 A2 | 1/2000 |
| WO | WO-2004/100763 A2 | 11/2004 |
| WO | WO-2006/047815 A1 | 5/2006 |
| WO | WO-2011/054045 A1 | 5/2011 |
| WO | WO-2011/156862 A1 | 12/2011 |
| WO | WO-2014/146693 A1 | 9/2014 |

OTHER PUBLICATIONS

Twan Basten Ambient Intelligence: Impact on Embedded System Design. Springer Science & Business Media 2007, p. 72-3.1 identification.
First Russian Office Action dated Mar. 15, 2017 issued in corresponding Russian patent application No. 2015145976 (8 pages) and its English-language translation thereof (7 pages).
Second Russian Office Action dated Oct. 5, 2017 issued in corresponding Russian patent application No. 2015145976 (6 pages) and its English-language translation thereof (5 pages).
Second Russian Office Action dated Jul. 5, 2017 issued in corresponding Russian patent application No. 2015145976 (6 pages) and its English-language translation thereof (5 pages).
Colombian Office Action Oficio N° 4978 dated Jul. 10, 2017 (13 pages) and its partial English-language translation thereof (10 pages).
Canadian Office Action dated May 17, 2017 issued in corresponding Canadian patent application No. 2 909 177 (6 pages).
Australian Examination report No. 1 dated Jan. 9, 2018 issued in corresponding Australian patent application No. 2017202242 (3 pages).
Canadian Office Action dated Apr. 10, 2018 issued in corresponding Canadian patent application No. 2,909,177 (5 pages).
Japanese Decision of Rejection dated Dec. 4, 2017 issued in corresponding Japanese patent application No. 2016-510944 (2 pages) and its English-language translation thereof (2 pages).
Australian examination report No. 2 dated May 30, 2018 issued in corresponding Australian patent application No. 2017202242 (6 pages).
First Chinese Office Action dated Apr. 3, 2018 issued in corresponding Chinese patent application No. 201380075688.3 (7 pages) and its English-language translation thereof (11 pages).
Second Chinese Office Action dated Nov. 21, 2018 issued in corresponding Chinese patent application No. 201380075688.3 (8 pages) and its English-language translation thereof (12 pages).
Australian examination report No. 3 dated Nov. 20, 2018 issued in corresponding Australian patent application No. 2017202242 (3 pp.).
Russian Decision on Grant dated May 23, 2018 issued in corresponding Russian patent application No. 2015145976 (11 pages) and its English-language translation thereof (7 pages).
Notice of Allowance dated Jun. 7, 2018 issued in corresponding Japanese patent application No. 2016-510944 (3 pages) and its partial English-language translation thereof (1 page).
Substantive examination adverse report dated Feb. 25, 2019 issued in Malaysian patent application No. PI 2015703608.
European Office Action dated Feb. 8, 2019 issued in European patent application No. 13 719 847.9.

* cited by examiner

DATA CAPTURE AND MANAGEMENT SYSTEM

CROSS-REFERENCE TO PRIOR APPLICATION

This application is a § 371 National Stage Application of PCT International Application No. PCT/EP2013/059037 filed Apr. 30, 2013, which is incorporated herein in its entirety.

TECHNICAL FIELD

The present disclosure relates to a data capture and management system for providing an absorbent article, such as a diaper, a sanitary towel, an incontinence garment, a medical dressing and the like, with sensing and/or datalogging capabilities.

TECHNICAL BACKGROUND

Absorbent articles, such as diapers, sanitary towels, incontinence garments, medical dressings and the like, have widespread utility in both domestic and institutional settings for such purposes as the care of infants, the management of menstrual discharge, the management of bodily efflux or exudate and the management of incontinence. However, a known problem associated with the use of absorbent articles is that the articles have a finite capacity for absorption, which, if exceeded, will cause the absorbent article to become ineffective, e.g. to leak, or at least to fail to absorb further.

Therefore, users of such articles, or their carers, must predict when an absorbent article is nearing its absorbent capacity and must then take steps to replace the article before capacity is reached. In situations where there are many users of such absorbent articles but relatively fewer carers, such as in institutional settings, the management of the capacity of the various absorbent articles in use becomes a significant administrative burden.

Since absorbent articles are available in a variety of absorbent capacities, the user or carer must also determine, from those products which are available, which capacity of article to select. For example, in some circumstances it may be preferable to select an article of a lower capacity which is changed more frequently in contrast to an article of relatively larger capacity which is changed less frequently. Factors influencing this choice will be the nature of the absorption required, i.e. whether intermittent large quantities or a continuous smaller rate, as well as the total volume expected to be absorbed during a given period of time.

It can be very difficult for a user or carer to accurately predict or determine the state of an absorbent article, in terms both of utilised absorbent capacity and the need for the article to be replaced. Even where the absorbent demands on the article are reasonably predictable, a period of record-keeping and experimentation is required before a pattern may be established, and appropriate absorbent articles provided.

Systems which are able to alert the user or carer to saturation or impending saturation of the absorbent article are therefore of benefit. Furthermore, systems which are able to monitor the usage pattern of a particular absorbent article, and of a series of absorbent articles associated with a particular individual, over a period of time, are of particular benefit.

Such systems may take the form of an absorbent article having embedded sensors which connect to a logger unit to monitor and record the sensor data over time. The sensors can, for example, be moisture sensors. When the absorbent capacity of the absorbent article is approached or exceeded, the user or the carer can be notified, on the basis of the recorded sensor data, that the absorbent article requires replacement.

Additionally, data obtained from a particular user over time can be used to monitor both the health of the user and the appropriateness of the absorbent article for that user over an extended period and can be used to provide better information for the care of the user. For example, an event, such as an incontinence event, leading to saturation of the article can be predicted and action, such as toileting action, taken before the event occurs.

Figure 1:
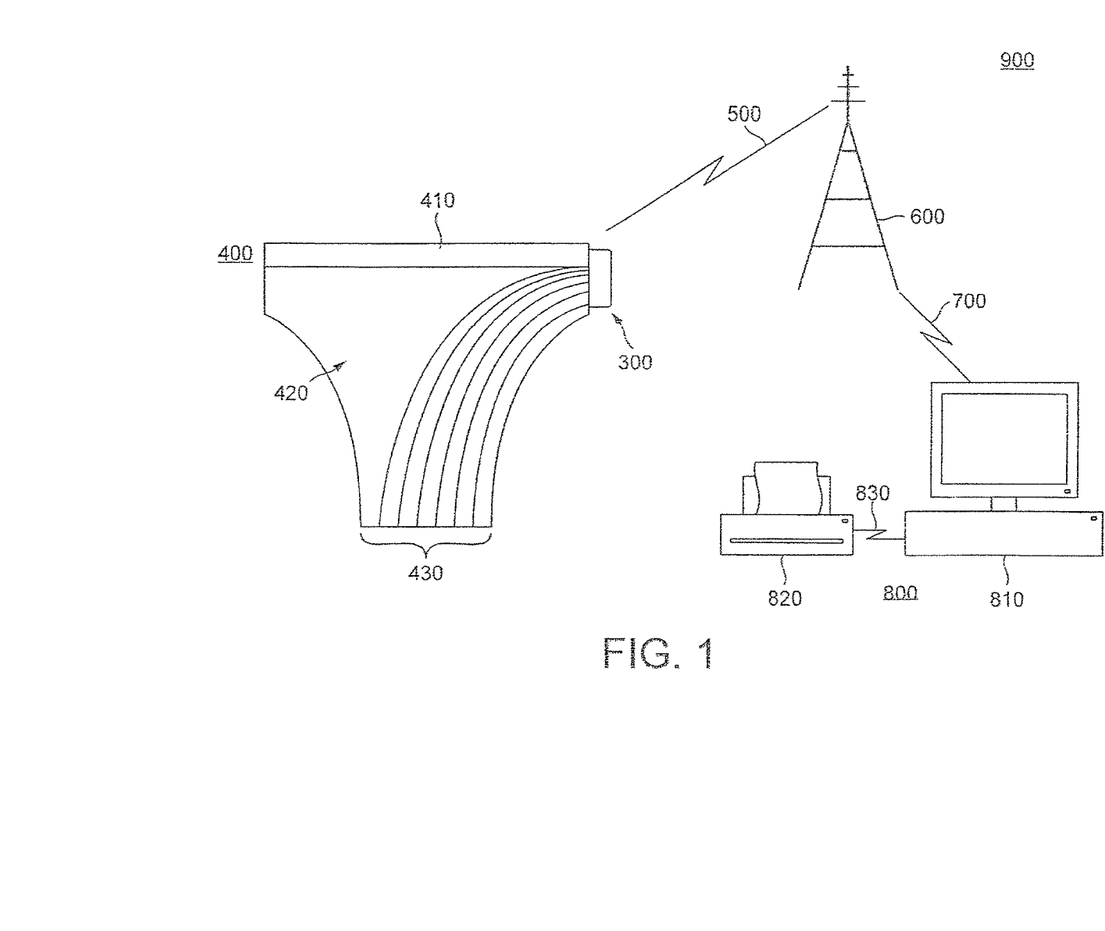
FIG. 1 shows an absorbent article provided with a logger unit and moisture sensing wires extending from the logger unit through the absorbent article.

One exemplary system is shown in FIG. 1, in which an absorbent article 400, exemplified here as a diaper and having a waistband 410 and an absorbent area 420, is provided with a logger unit 300 attached to the waistband 410 and having sense wires 430 extending from the logger unit 300 running through the absorbent area. The sense wires 430 may be used to detect moisture, for example by detecting changes in the conductivity between the wires. The sense wires may be only partly exposed to the absorbent area, for example by providing insulation, to localise the region of sensing. The particular wiring pattern depicted is wholly exemplary, and will be selected according to the sensing requirements.

The logger unit 300, including data-logging electronics such as a power source, processor, memory, instruction store, data store, communications bus, and data link interface, which cooperate to store, process, and/or forward the data derived from sense wires, is connected by data link 500 to a data receiver 600. In the example of FIG. 1, data link 500 is a wireless data link, and data receiver 600 is a wireless data receiver. However, it is also possible that a docking functionality can be provided between the logger 300 and a docking station functioning as data receiver 600 to transfer data recorded in the logger 300 when the logger 300 is placed into the docking station. In a further alternative, data link 500 can be provided over the cellular telephone network, in which case data receiver 600 may be implemented as a cellular base station.

The data received at data receiver 600 is then transmitted by a further data link 700 to data processing equipment 800, exemplified as computer terminal 810 and output device 820 mutually connected by data link 830. Here, the computer terminal 810, which is an example of a general purpose data processing device, conducts processing on the sensor data received from the logger unit 300 via data links 500 and 700 and data receiver 600 and takes action based on the same, for example by outputting alerts, predictions, or statistics via output device 820. Here, the output device is shown as a line printer, but could, for example, be another form of hard copy printer, a visual display unit, a visual alarm panel, or an audio output device, without limitation.

Such a system may provide a powerful tool for the management of users of absorbent articles.

However, absorbent articles are conventionally disposable absorbent articles for reasons of hygiene and convenience. Although reusable absorbent articles are known, they are rarely used, especially in institutional and clinical settings, for reasons of economy and hygiene, amongst others.

Therefore, in the arrangement of FIG. 1, if the logger unit 300 is directly connected to sensor wires 430, which extend through the article 400, when the absorbent article 400 is to be discarded after a use, the logger unit 300 must be discarded also. As the logger unit 300 is generally far more costly than the article 400 to manufacture, it is advantageous to provide the absorbent article 400 with a receptacle for receiving the ends of the sensor wires 430 at conductive terminals, and for accommodating the logger unit in a manner which permits the conductive terminals of the receptacle to contact corresponding conductive terminals of the logger unit when the logger unit is engaged with the receptacle. Such an arrangement is disclosed in Applicants' International Patent Application PCT/EP2013/055686, which was filed on 19 Mar. 2013. In this manner, when an absorbent article is ready for disposal, the data logger can simply be disengaged from the receptacle by the care giver, and then engaged with the receptacle attached to the new absorbent article. This ensures that, when a new diaper is provided to an end user, the same logger is used so there is no potential for confusion regarding which data pertains to which end user.

However where many data loggers are distributed to various end users, such as in a care institution or hospital, the caregiver needs to ensure that when a logger is provided to an end user, the logger is correctly initialized and that data linking the logger to the end user are correctly recorded. This provides a data management challenge which is addressed by the present invention.

SUMMARY

Although the data link can take any known form of data link, it is advantageous that the data be transmitted via a wireless network such as a wireless local area network (WLAN/WiFi) or a cellular telephone network, for example.

Each data logger is identifiable by a unique device identifier. The unique device identifier is assigned by the manufacturer of the device or the network controller and follows the international standard for that device. For example, where a data logger is configured to transmit data via a cellular telephone network, the data logger includes a modem having an IMEI number, unique to that modem. All devices which use a cellular telephone network to transmit data are identified by a unique 15-digit number—the IMEI number (International Mobile Station Equipment Identity number). The IMEI number is an international standard recognized by the cellular telephone networks. The IMEI number is used to identify a particular device.

Similarly, wireless local area networks use a MAC (Media Access Control) address as the unique device identifier, rather than the IMEI number. A MAC address is six groups of two hexadecimal digits, optionally separated by hyphens or colons, to identify that particular device.

For cellular telephone networks, it is also possible to use the IMSI (International Mobile Subscriber Identity) number, which is globally unique to the SIM card, rather than the IMEI, which is globally unique to the hardware. Of course, if the SIM card is changed then the device identifier will also change, and for this reason it may be preferable to use the IMEI number of the hardware rather than the IMSI number to identify the data logger where a cellular telephone network is used as the data link.

Data transmitted by a data logger will also include the unique device identifier of the transmitting device and the date and time of transmission of the data package. This allows all the data sent from a particular device during a particular time period to be identified. The data may be transmitted from the data logger to a central server, which stores information received from several data loggers.

As the unique device identifiers conform to global international standards, they tend to be very long. For example, the IMEI number is 15 digits long, is not easy to remember and so is considered a non-user-friendly number. Therefore, requiring a caregiver to correctly remember or accurately note this number when assigning a logger to a user is likely to lead to data management errors.

According to one aspect there is provided:

an incontinence data capture and management system including:

a data logger configured to be detachably attached to or located in the vicinity of an absorbent article, a data link between the data logger and a data collection hub, a user interface for permitting an operator to access the data collection hub from a remote location, the data logger being configured to transmit a data package to the data collection hub at predetermined intervals, the data package including a unique device identifier of the data logger, wherein the data logger is further provided with a user-friendly identifier, and the data collection hub includes correlation means for correlating the user-friendly identifier of the data logger with the unique device identifier of that data logger.

Advantageously, the user interface is configured to permit the operator to associate a particular data logger with a particular individual by use of the user-friendly identifier.

The data logger may be in direct contact with the absorbent article. The data logger may be detachably attached to a receptacle located on the absorbent article as described in PCT/EP 2013/055686. Alternatively, the data logger may be located in the vicinity of the absorbent article. For instance, if the sensor is a gas sensor instead of sensor wires, the sensor and data logger can be located proximate to, but not in contact with, the absorbent article.

In particular embodiments, the data link is a cellular telephone network.

In certain embodiments, the unique device identifier is an IMEI number.

The data collection hub may be a server located remotely from the data logger and/or the user interface.

The correlation means may be a look-up table.

Advantageously, several data loggers may be provided, each data logger being adapted to transmit data to the data collection hub by the cellular telephone network. In certain embodiments, each data logger has a unique user-friendly identifier which is visible on an outer cover of the data logger. A plurality of user interfaces may also be provided. One or more data loggers may be associated with each of the user interfaces. The user interface can be, for example, a web-based interface for allowing an operator to access the data collection hub over the interne.

In certain embodiments, the user-friendly identifier includes fewer than five characters. Advantageously the user-friendly identifier includes two or three alphanumeric characters. The user-friendly identifier may include a letter and two numbers for example.

The system may further include one or more charging units for charging the one or more data loggers.

The user interface may be located proximal to, or alternatively remotely from, its associated one or more data loggers.

In particular embodiments, each data logger is configured to store data until the data logger receives a signal from the data collection hub confirming that the data has been successfully transmitted to the data collection hub.

According to another aspect, there is provided:

a method of capturing and managing incontinence data including:

providing a user interface for permitting an operator to access a data collection hub from a remote location, configuring one or more data loggers to transmit a data package to the data collection hub at predetermined intervals, the data package including a unique device identifier of the data logger, marking each data logger with a user-friendly identifier, correlating the user-friendly identifier with the unique device identifier of the data logger, and supplying a user with one or more marked data loggers, and a web-based interface for accessing the data collection hub.

The data collection hub receives, via the data link, the data packages from each of the data loggers. The data collection hub uses the unique device identifier to identify the user-friendly identifier of the data logger. The data collection hub collates data received from each data logger, and the user accesses the data received from each data logger by providing its user-friendly identifier, via the web-based user interface.

In particular embodiments, the method includes the further step of providing the user with instructions to input the start and finish time of use of each data logger, and a further personal identifier for identifying the end user of the data logger, via the web-based user interface.

BRIEF DESCRIPTION OF THE DRAWINGS

Embodiments of the invention will now be described by way of example only and with reference to the following drawings.

DETAILED DESCRIPTION OF PARTICULAR EMBODIMENTS

Figure 2:
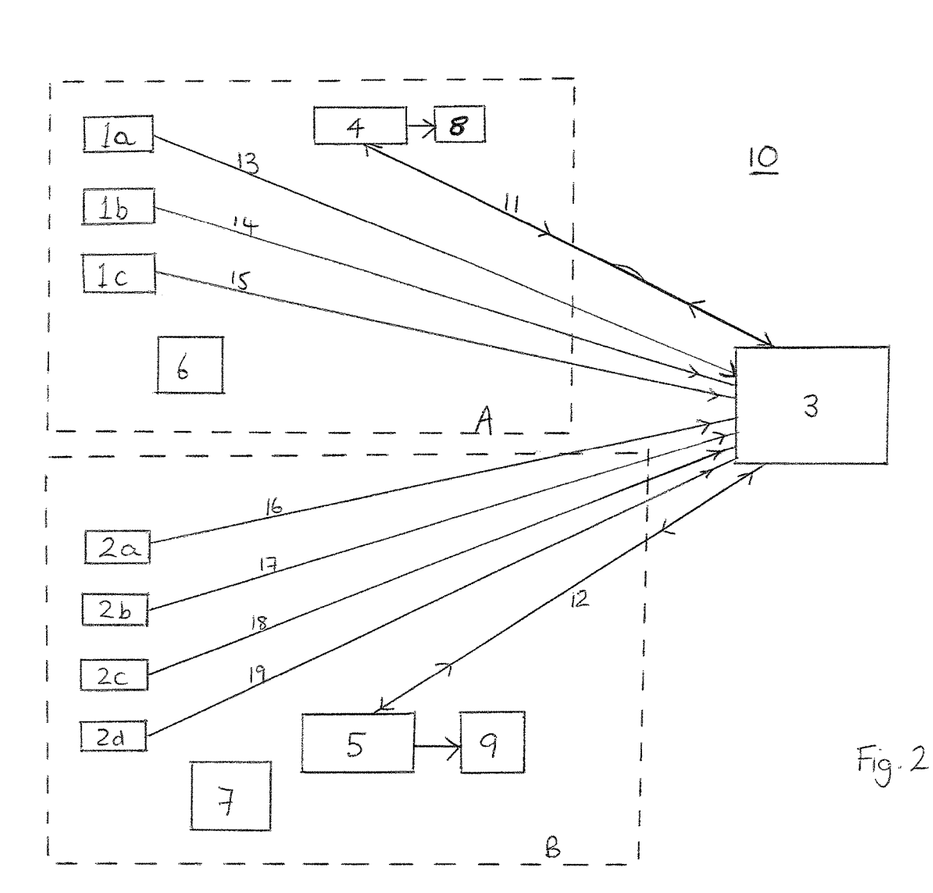
FIG. 2 shows an incontinence data capture and management system in accordance with an embodiment of the present invention.

FIG. 2 shows a system 10 including a plurality of data loggers 1a to 1c and 2a to 2d, a data collection hub 3 and user hardware 4 and 5. Data loggers 1a to 1c are supplied to one user, for example a nursing home, represented by the dotted line A. The nursing home also has hardware for accessing the internet 4, for example a computer, a laptop, a tablet device, or a cellular telephone device with internet access. Optionally the hardware 4 is connected to a display 8, which could be a monitor or a printer for example.

The user is able to access the data collection hub 3 via the computer 4 and web user interface 11.

Data loggers 1a to 1c are each configured to log data continuously and to send the data package to the data collection hub at predetermined intervals. The data loggers 1a to 1c transmit the data packages over data links 13 to 15, respectively. The data loggers use the cellular telephone network to transmit data to the data collection hub, and each has a unique 15-digit IMEI number which identifies the individual data logger. The date and time of logging of the data and IMEI number of the data logger are transmitted with each package of data Each of data loggers 1a to 1c are assigned to a different end user, i.e. three residents of the nursing home. The web user interface permits the staff at the nursing home to record which data logger has been assigned to which resident. Instead of using the names of the residents, to ensure privacy the nursing home may identify the residents by their initials, their room number, or some other identifying code.

As the IMEI number is very long and difficult to remember, to improve the accuracy of the data management system an individual three-character identifier has been allocated to each data logger prior to dispatch of the data loggers to the nursing home.

For example, the data loggers 1a to 1c may be given the user-friendly identifiers A01 to A03, respectively. Of course, a single letter or number or two characters may be used instead, but three characters is advantageous as explained below. The data loggers are marked with the user-friendly identifiers prior to dispatch. The markings may be laser-etched or engraved on the outer casing of the data logger, or a label bearing the user-friendly identifier may be applied onto the outer casing of the data logger, for example. The MEI number of each data logger is correlated with the user-friendly identifier and this information is stored in or made available to the data collection hub 3.

Upon receipt of the data loggers, the staff at the nursing home allocates each data logger to a resident. Using their own computer and internet access, they can access the data collection hub via a web user interface. The system is configured such that the nursing home staff can only access data relating to the data loggers that are allocated to that nursing home (in this case loggers 1a to 1c and not loggers 2a to 2d which are described further below) and only for the time period for which they are allocated to that nursing home. The data is password protected. These data access techniques are well-known.

The nursing home staff, using the web user interface, matches each of their data loggers with a resident, using the user-friendly identifier to identify the data logger, and the name, initials or other identifying code of the resident. Ideally, the nursing home staff also indicates the time period for which the data logger will be allocated to that resident.

The data logger is then attached to the incontinence pad, diaper or other absorbent article worn by the resident. It continuously logs information and, at the predetermined time intervals, uses the cellular telephone network to transmit a data package to the data collection hub. The data package is identified by the IMEI number of the data logger, and the data collection hub collates all of the data packages received from an individual data logger.

If, for some reason, the data logger is not able to transmit a data package at a predetermined time interval, the data logger continues to record data and then attempts to transmit all the recorded data at a later time. In this manner, no data is lost. Once the data collection hub receives and acknowledges the data package, the data logger is able to delete the recorded data and continues to continuously record new data.

The nursing home staff is able to access the data collated by the data collection hub for a particular data logger at any time, and can download, manipulate and print the date as required. In this manner, the wetting profile of a resident can be analyzed and an individual plan to manage his needs can be formulated.

To access the data, the nursing staff uses the user-friendly identifier to identify the data logger, or alternatively the resident's identifying code. The data collection hub identifies which MEI number is associated with that user-friendly identifier or resident's identifying code, and provides the appropriate collated data.

If a data logger becomes faulty, or if it is desired that data be recorded during the periods when a logger assigned to an end user is charging, a second data logger can be allocated to an end user. For example, data loggers 2a to 2d are assigned to a hospital, and each of the data loggers 2a to 2c are respectively allocated to particular patients. Data loggers 2a to 2c transmit data at predetermined intervals to data collection hub 3 over the cellular telephone network. Within the hospital, denoted by the dotted line B, a computer 5 connected to the internet is provided. The computer 5 is optionally linked to a display device 9 such as a monitor or printer, for example. The hospital nurses are able to access the data collection hub 3 by using computer 5 via web interface 12.

Prior to dispatch of the data loggers to the hospital, each data logger is marked with an individual user-friendly identifier, and these identifiers are correlated with the IMEI number of the data loggers in a look-up table held on the data collection hub server. Upon receipt by the hospital, each data logger 2a to 2c is allocated to a particular patient. Data logger 2d is held in reserve. If one of the data loggers 2a to 2c becomes faulty, the hospital staff connect to the data collection hub 3 over the web interface 12, and alter the data associated with the affected patient. The user-friendly identifier of the patient's data logger is simply changed by the hospital staff to reflect the user-friendly identifier of the new data logger 2d, the physical data logger on the patient is replaced by the data logger 2d, and data logger 2d continues to log data pertaining to the patient. When the patient's incontinence data is accessed by the hospital staff, this data will be a collation of the data received from the initial data logger during the period when it was operational, combined with the data received during the later period from the replacement data logger 2d. This ensures that accurate data is received from the patient, even in the event of a data logger fault.

Similarly, if it is desired that data be recorded during the periods when the patient's original data logger is charging using charger 7, the replacement data logger 2d can be used during these charging periods. To ensure the integrity of the data, the hospital staff should indicate, via the web interface, which data logger was associated with the patient during which particular periods of time.

It can therefore be seen that, even if different data loggers are used for a particular patient, or if data loggers are re-assigned to new patients, the data can be managed effectively and accurately. By providing the data loggers with a 3-digit user-friendly identifier, there is no need for nursing staff to deal with the long 15-digit IMEI number, which is difficult to remember, and can easily be noted incorrectly.

A 3-character alphanumeric user-friendly identifier can be preferred, because this allows a large number of data loggers to be marked with unique user-friendly identifiers. As the data loggers are allocated user-friendly identifiers and marked with these centrally, before being sent out to users, such as nursing homes and hospitals. Providing unique identifiers makes it much easier for the service provider to manage the data loggers, particularly when individual data loggers might be sent to various hospitals and nursing homes during their lifetime. It is generally easier for humans to remember letters than numbers, however, providing three different letters would, although leading to a greater number of potential user-friendly identifiers, open the system to ridicule in situations where an unfortunate combination of three letters were used. For this reason, it is probably best to allocate one letter and two numbers, or possibly two letters and one number, as the user-friendly identifier.

Figure 3:
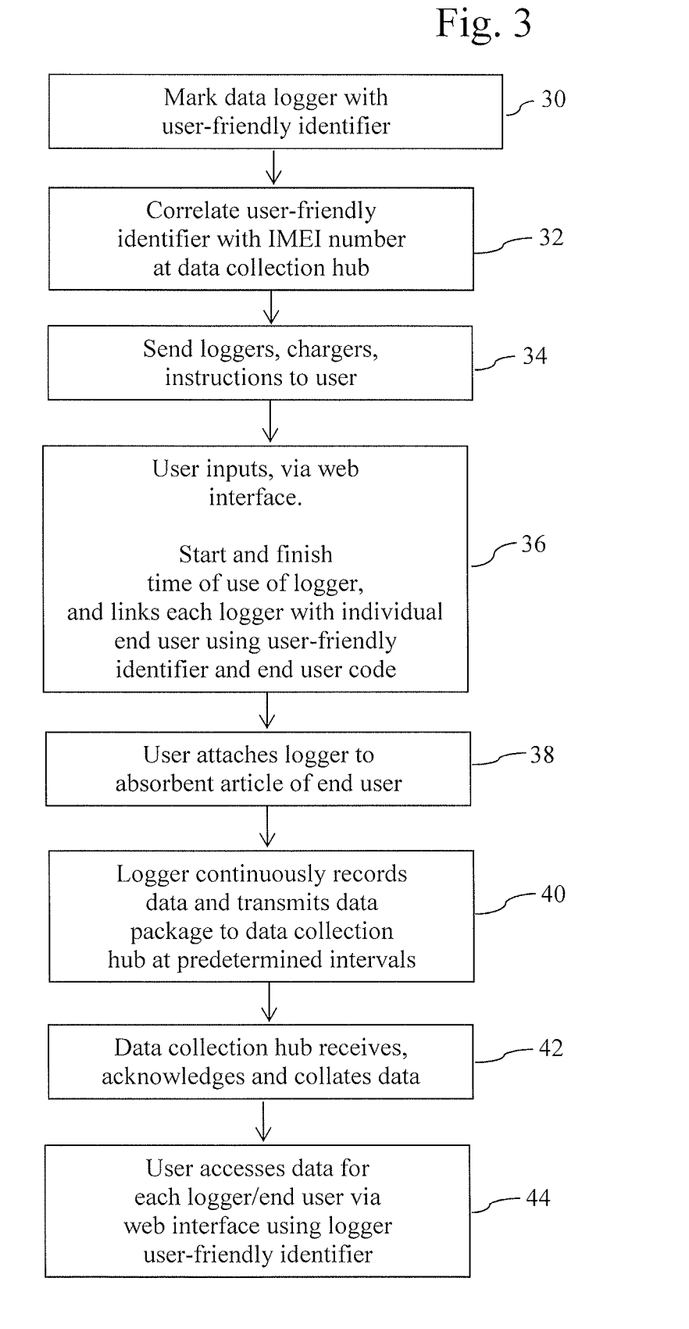
FIG. 3 shows a method of capturing and managing incontinence data in accordance with an embodiment of the present invention.

FIG. 3 shows a flowchart setting out a method of capturing and managing incontinence data in accordance with an embodiment of the present invention. The data management system provider marks each of his data loggers with a user-friendly identifier (30), for example by engraving or laser etching the user-friendly identifier on to the outer cover of the data logger. This ensures that anyone using the data logger can easily see the user-friendly number, and the user-friendly number cannot easily be accidentally removed. Before sending the data loggers to a customer, the data management system provider correlates the user-friendly identifier of each data logger with its corresponding IMEI number at the server acting as the data collection hub (34). This can be done in the form of a database or other type of look up table which is either stored within the data collection hub server or is stored in an area to which the data collection hub server has access. The data loggers, along with one or more data logger chargers for charging the batteries of the data loggers, are then sent to the customer along with operating instructions (32). The customer may be a nursing home, a hospital, or an individual, for example.

Upon receiving the data loggers, the customer is able to access the data collection hub server via a web interface provided by the data management system provider. His data is password protected, and he is only able to access the data supplied by the data loggers allocated to him, for the period for which the loggers are/were allocated to him. This ensures that privacy is maintained, even when the data loggers are allocated, at various times, to various customers.

The customer is able to provide the data collection hub with various information, as he desires. For example, where a customer has taken delivery of several data loggers intended for distribution to several end users such as hospital patients, to enable the data to be managed effectively the customer might link each of his data loggers with a particular patient, using the user-friendly identifier to identify the data logger, and using the patient's initials or room number, for example, to identify the patient who has received that particular data logger. The customer may also indicate the period of time that the data logger was used by the patient (38).

The data logger can be attached to the absorbent article worn by the patient (38), either before, after or during the activity indicated by reference numeral (36) above. The logger continuously records data and transmits a package of data to the data collection hub at predetermined intervals, over a cellular telephone network (40). The data collection hub receives the data packages from each data logger, and is able to identify and collate data received from an individual data logger by using the IMEI number of that logger which is transmitted with each data package (42). When he desires, the customer is able to access the data relating to a particular data logger/particular patient via the web interface (44) by selecting the user-friendly identifier of that data logger, or by selecting the particular patient if the customer has previously linked each patient with one or more data loggers.

It can therefore be seen that the system of embodiments of the present invention provides an easy way to capture incontinence data relating to different patients. As the data is transmitted over the cellular phone network, the patient is free to leave the hospital, if desired, without jeopardizing the integrity of the data. Wherever the patient is, the data is able to be transmitted back to the data collection hub, as long as there is a cellular network signal. Even if the patient is located in an area where there is no cellular phone signal, the data logger will continue to continuously record data until such time as the patient returns to an area where there is network coverage. At this point, the data logger will transmit the data to the data collection hub at the predetermined time interval, and thereafter the data will be captured and transmitted as usual. Even if the nursing home or hospital does not have cellular network coverage, the data logger may be used for the period of the incontinence analysis, and the data logger may then be detached from the patient and sent either back to the provider of the data loggers, or to another location, such as a sister hospital or nursing home, where there is network coverage. At this new location the data logger can then transmit the data logged during the period that it was connected to that particular patient.

Embodiments of the present invention also are advantageous in that no hardware or software, other than the data loggers and chargers, needs to be sent to the nursing home or hospital. The data collection hub can be accessed via a web interface from any PC, laptop, tablet device or cellular telephone, for example, which has internet access, and therefore specialist equipment need not be provided. Furthermore, on-site support is not required as the software is installed at the data collection hub, and not at the user's site. Even if there is a period where the data collection hub is unavailable, such as for server maintenance, the individual data loggers continue to log and store data until this data has been transmitted successfully. Therefore, even if the data collection hub server is not available for a period of time, there is no loss of patient data.

Although embodiments of the present invention have been described with respect to hospitals and nursing homes, it can be appreciated that this invention might be used in any setting where the capturing and management of incontinence data is required, such as in the home of an individual user, for example.

The invention claimed is:

1. An incontinence data capture and management system comprising:
    a data logger configured to be detachably attached to or located in the vicinity of an absorbent article;
    a data link between the data logger and a data collection hub; and
    a user interface that permits an operator to access the data collection hub from a remote location,
    the data logger being configured to transmit a data package to the data collection hub at predetermined intervals, wherein the data logger has a unique device identifier that identifies the data logger and wherein the data package includes the unique device identifier of the data logger,
    wherein the data logger is visibly marked with a user-friendly identifier that identifies the data logger, and the data collection hub correlates the user-friendly identifier of a data logger with the unique device identifier of that data logger, and wherein the user-friendly identifier has less alphanumeric characters than the unique device identifier.

2. The incontinence data capture and management system as claimed in claim 1, wherein the user interface is configured to permit the operator to associate a particular data logger with a particular individual by use of the user-friendly identifier.

3. The incontinence data capture and management system as claimed in claim 1, comprising several data loggers, each data logger being adapted to transmit data to the data collection hub via the data link.

4. The incontinence data capture and management system as claimed in claim 1, wherein the data link is a cellular telephone network and the unique device identifier is the IMEI number or the IMSI number.

5. The incontinence data capture and management system as claimed in claim 1, wherein the data collection hub is a server located remotely from the data logger and/or the user interface.

6. The incontinence data capture and management system as claimed in claim 1, wherein the user-friendly identifier is visible on an outer cover of the data logger.

7. The incontinence data capture and management system as claimed in claim 1, comprising a plurality of user interfaces.

8. The incontinence data capture and management system as claimed in claim 7, wherein one or more data loggers is associated with each of the user interfaces.

9. The incontinence data capture and management system as claimed in claim 1, wherein the user interface is a web-based interface that allows an operator to access the data collection hub over the internet.

10. The incontinence data capture and management system as claimed in claim 1, wherein the user-friendly identifier comprises fewer than five characters.

11. The incontinence data capture and management system as claimed in claim 1, wherein the user-friendly identifier comprises two or three alphanumeric characters.

12. The incontinence data capture and management system as claimed in claim 1, wherein the system further comprises one or more charging units that charge the one or more data loggers.

13. The incontinence data capture and management system as claimed in claim 1, wherein each data logger is configured to store data until the data logger receives a signal from the data collection hub confirming that the data has been successfully transmitted to the data collection hub.

14. A method of capturing and managing incontinence data comprising:
    providing a user interface that permits an operator to access a data collection hub from a remote location;
    configuring one or more data loggers to transmit a data package to the data collection hub at predetermined intervals, wherein each of the one or more data loggers has a unique device identifier that identifies the corresponding data logger and wherein the data package includes the unique device identifier of the corresponding data logger, and wherein the data collection hub receives, via a data link, the data packages from each of the data loggers;
    visibly marking each of the one or more data loggers with a user-friendly identifier that identifies the corresponding data logger, wherein for each of the one or more data loggers the user-friendly identifier has less alphanumeric characters than the unique device identifier for the same data logger;
    for each of the one or more data loggers, correlating the user-friendly identifier of the data logger with the unique device identifier of the same data logger;
    supplying a user with one or more of the one or more marked data loggers, and a web-based interface for accessing the data collection hub; and
    using the data collection hub to identify the user-friendly identifier of the data logger from the unique device identifier of the same data logger, to collate data received from each data logger, and to provide, via the user interface, access to the data received from each data logger by the user providing the user-friendly identifier of the data logger.

15. The method of capturing and managing incontinence data as claimed in claim 14, further comprising providing the user with instructions to input the user-friendly identifier marked on the data logger, the start and finish time of use of the data logger, and a further personal identifier for identifying the end user of the data logger, via the user interface.

16. An incontinence data capture and management system comprising:
- a data logger configured to be detachably attached to or located in the vicinity of an absorbent article;
- a data link between the data logger and a data collection hub; and
- a user interface that permits an operator to access the data collection hub from a remote location,
- the data logger being configured to transmit a data package to the data collection hub at predetermined intervals, wherein the data logger has a unique device identifier that identifies the data logger and wherein the data package includes the unique device identifier of the data logger,
- wherein the data logger is visibly marked with a user-friendly identifier that identifies the data logger, the user-friendly identifier being shorter than the unique device identifier,
- wherein the data collection hub is configured to collate data packages received from different data loggers used for the same user, each data logger being identifiable in the data collection hub by a respective user-friendly identifier correlated to a respective unique device identifier, and
- wherein when the operator accesses, via the user interface, the data collection hub using a user-friendly identifier of a data logger, the data collection hub is configured to provide data, collated by the data collection hub, from the data logger and other data loggers relating to the same user for access by the operator.

17. The incontinence data capture and management system as claimed in claim 16, wherein the user interface is configured to permit the operator to associate a particular data logger with a particular individual by use of the user-friendly identifier.

18. The incontinence data capture and management system as claimed in claim 16, wherein the data link is a cellular telephone network and the unique device identifier is the IMEI number or the IMSI number.

19. The incontinence data capture and management system as claimed in claim 16, wherein the user interface is a web-based interface that allows an operator to access the data collection hub over the internet.

20. The incontinence data capture and management system as claimed in claim 16, wherein each data logger is configured to store data until the data logger receives a signal from the data collection hub confirming that the data has been successfully transmitted to the data collection hub.

* * * * *

UNITED STATES PATENT AND TRADEMARK OFFICE
CERTIFICATE OF CORRECTION

PATENT NO. : 10,425,301 B2
APPLICATION NO. : 14/787283
DATED : September 24, 2019
INVENTOR(S) : Christer Olofsson Ranta, Sofia Hermansson and Anna Granberg Page 1 of 1

It is certified that error appears in the above-identified patent and that said Letters Patent is hereby corrected as shown below:

On the Title Page

Item [72], Delete "Christer OLOFFSON RANTA" and insert --Christer OLOFSSON RANTA--

Signed and Sealed this
Tenth Day of December, 2019

Andrei Iancu
*Director of the United States Patent and Trademark Office*